United States Patent
Nichols

(10) Patent No.: US 7,038,201 B2
(45) Date of Patent: *May 2, 2006

(54) METHOD AND APPARATUS FOR DETERMINING ELECTRICAL CONTACT WEAR

(75) Inventor: Bruce W. Nichols, Dallas, TX (US)

(73) Assignee: Nichols Applied Technology, LLC, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/896,689

(22) Filed: Jul. 22, 2004

(65) Prior Publication Data

US 2004/0256551 A1    Dec. 23, 2004

Related U.S. Application Data

(63) Continuation-in-part of application No. 10/318,859, filed on Dec. 13, 2002, now Pat. No. 6,884,998.

(51) Int. Cl.
*H01H 33/75* (2006.01)
*H01H 33/82* (2006.01)

(52) U.S. Cl. .................. 250/302; 250/295; 250/484.2; 250/461.1

(58) Field of Classification Search ............... 250/259, 250/260, 302, 461.1, 484.2, 295
See application file for complete search history.

(56) References Cited

U.S. PATENT DOCUMENTS

| | | | |
|---|---|---|---|
| 4,409,993 A * | 10/1983 | Furihata | 607/116 |
| 4,532,499 A | 7/1985 | Collin et al. | |
| 4,929,837 A | 5/1990 | DiVita et al. | |
| 5,200,615 A | 4/1993 | Hopenfeld | |
| 5,453,591 A | 9/1995 | Stroud | |
| 5,941,370 A | 8/1999 | Nichols | |
| 6,023,036 A | 2/2000 | Nichols | |
| 6,231,227 B1 | 5/2001 | Andersen | |
| 6,361,205 B1 | 3/2002 | Andersen | |
| 6,466,023 B1 | 10/2002 | Doughrty et al. | |
| 6,884,998 B1 * | 4/2005 | Nichols | 250/302 |
| 2003/0071212 A1 | 4/2003 | Weiland et al. | |

* cited by examiner

*Primary Examiner*—Nikita Wells
*Assistant Examiner*—David A. Vanore
(74) *Attorney, Agent, or Firm*—Winstead Sechrest & Minick P.C.

(57) ABSTRACT

A fluorescent trace material is provided within at least a portion of an electrical contact or interrupter assembly component, or a cavity defined therein. At least a portion of the fluorescent trace material is exposed or released from the electrical contact or interrupter assembly component, indicating a degree of component wear.

11 Claims, 8 Drawing Sheets

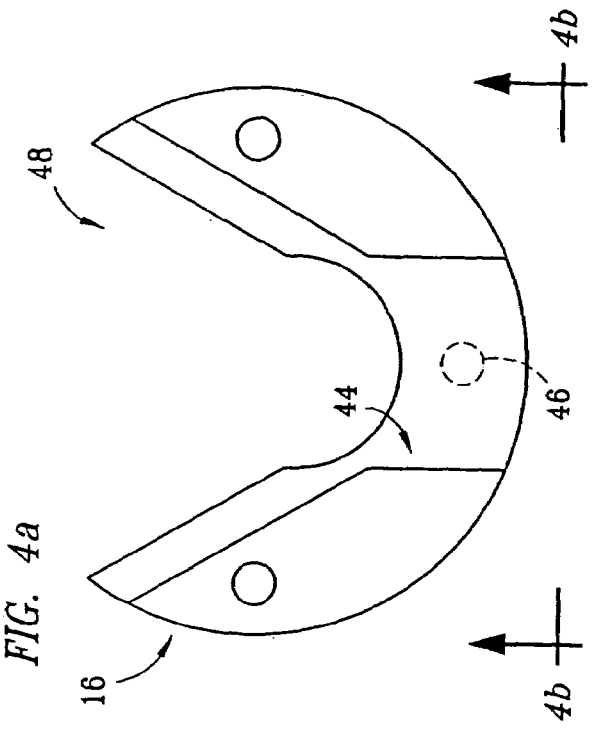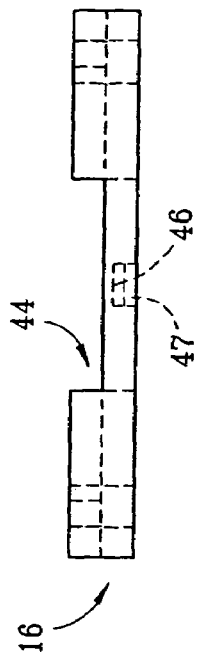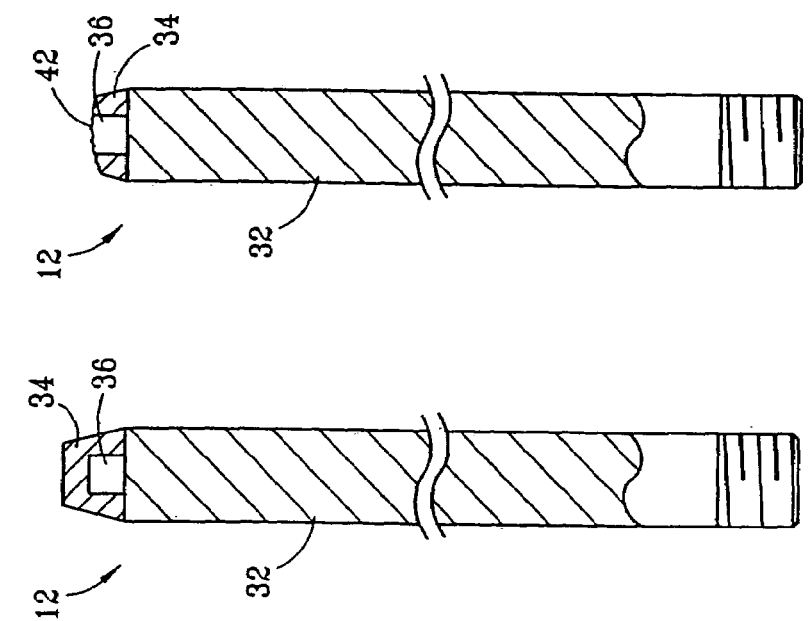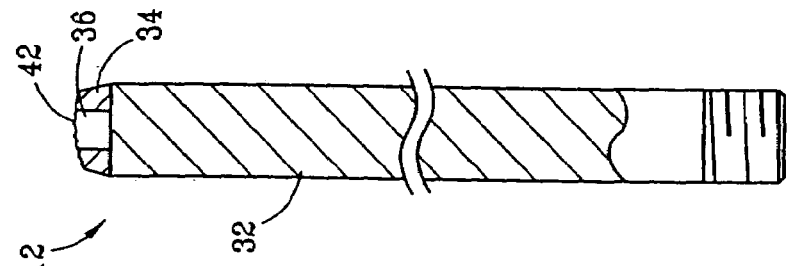

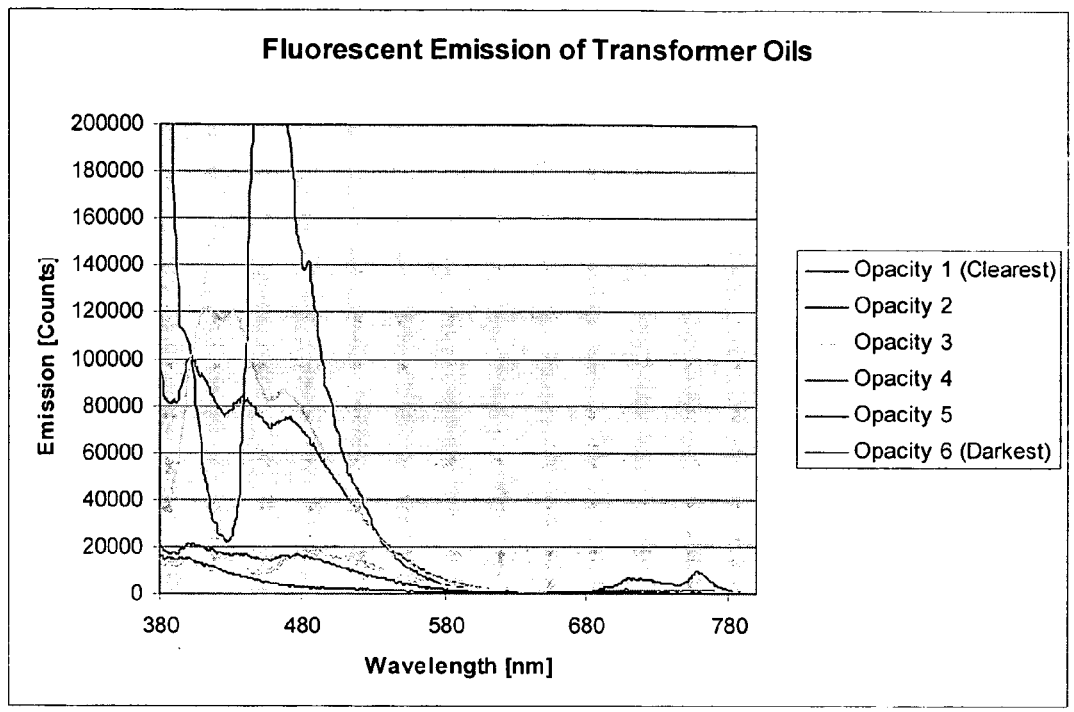
Figure 12: Emission spectra of oil samples
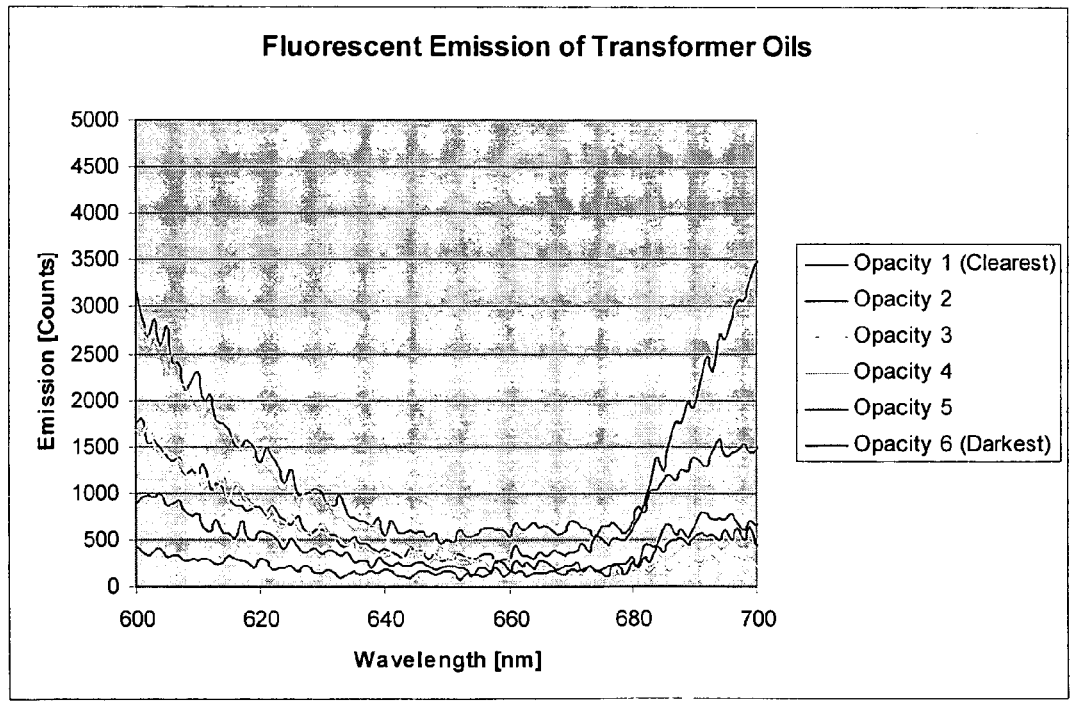
Figure 13: Emission spectra of oil samples at emission minima

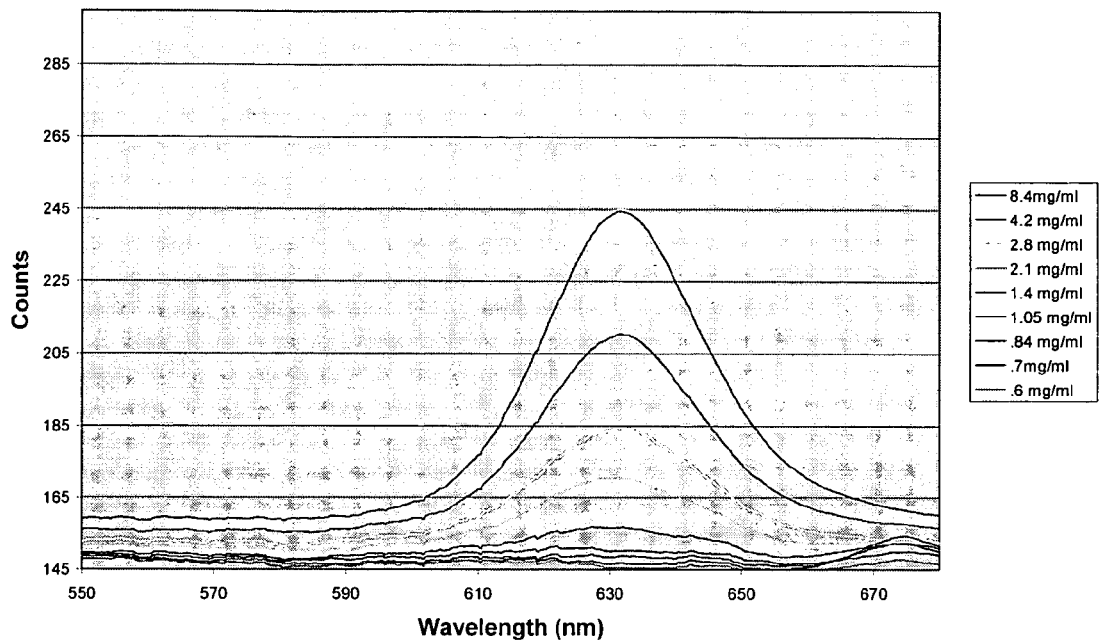
Figure 14: Emission spectra of Opacity 6 oil doped with various concentrations of fluorescent trace materials
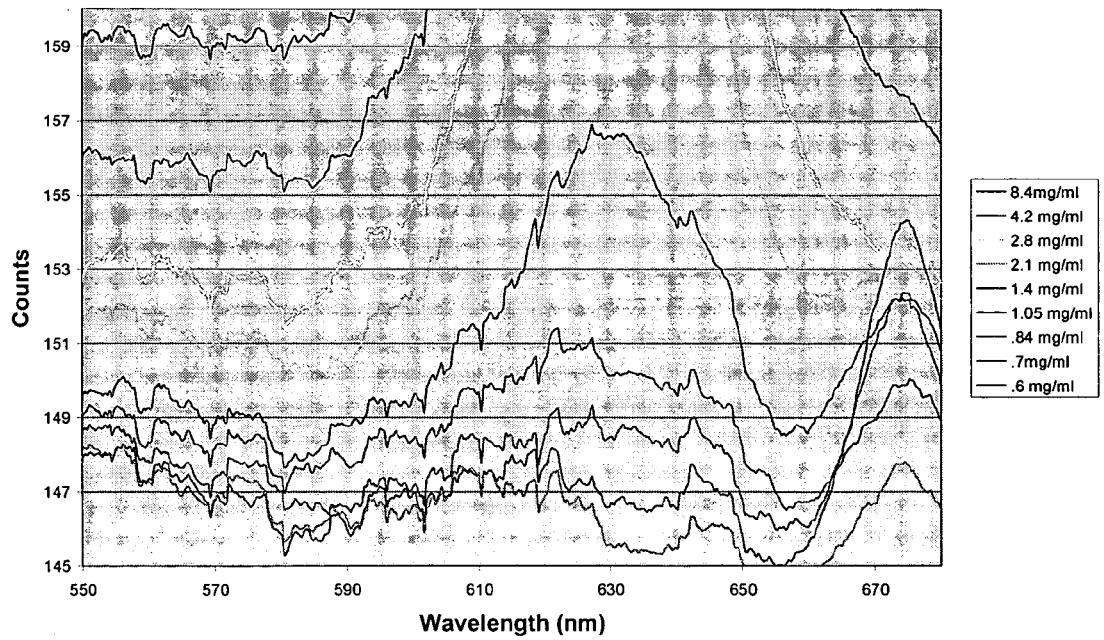
Figure 15: Emission spectra of dilute oil samples

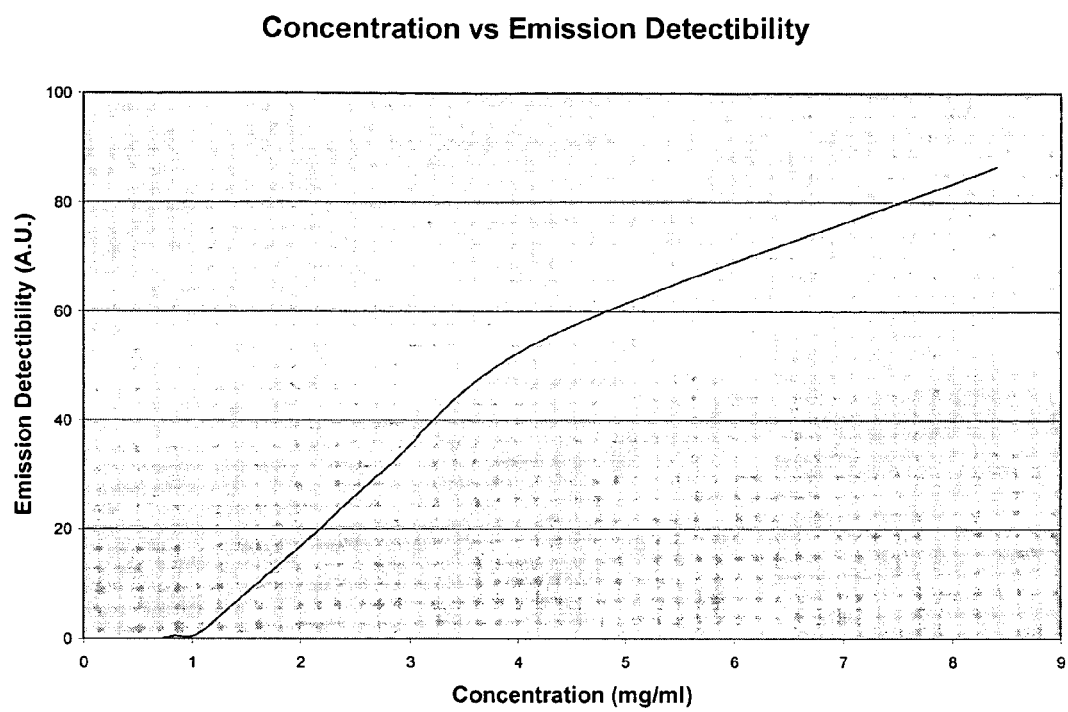
Figure 16: Strength of emission at Nanocrystal emission peak versus concentration.

METHOD AND APPARATUS FOR DETERMINING ELECTRICAL CONTACT WEAR

CROSS-REFERENCE TO RELATED APPLICATION

This application is a continuation in part of U.S. Ser. No. 10/318,859, filed on Dec. 13, 2002, now U.S. Pat. No. 6,884,998 entitled METHOD AND APPARATUS FOR DETERMINING ELECTRICAL CONTACT WEAR, by inventor Bruce Nichols.

FIELD OF INVENTION

The present invention relates in general to electrical switching mechanisms ("switches") and in particular to detecting the extent of erosion or wear of electrical contacts and arc interrupter assembly ("interrupter assembly") components caused by arcing or other wear processes and/or mechanisms, including but not limited to mechanical wear.

BACKGROUND OF INVENTION

A variety of electrical equipment contains switches which interrupt or direct the path of electricity through an electric circuit. Circuit breakers, for example, are switches used to open a circuit in the event of a fault, short circuit or similar breaks in current or to intentionally isolate equipment for inspection or maintenance. Another type of switch is a load tap changer, which is used to automatically select a particular tap corresponding to a connection within the secondary windings of a transformer in order to increase or decrease the amount of voltage transformation required as loading conditions change.

The parts of a switch which actually perform the function of connecting and disconnecting the current path are called electrical contacts ("contacts"). In high voltage equipment, the contacts of electrical switches operating under load generally erode over time during normal operation. The erosion of electrical contacts most commonly results from the arcing that occurs whenever a switch breaks, or interrupts, a circuit. An arc is formed as the electrical contacts move apart from or toward each other and the electro motive potential between them causes electrons to bridge the inter-contact space region with a corresponding electrical discharge. A current is maintained in the arc until the spacing between the contacts, and thus the impedance increases enough to prevent electrons from bridging the gap for the given voltage potential, or, if moving toward each other, until the contacts are touching. As well, current flowing across the gap generates extreme heat, resulting in temperatures high enough to burn away some of the contact material.

Erosion of the contacts can cause respective mechanism failures or deteriorated switch operation, and otherwise generally reduce or limit the useful lives of the switches themselves. Switches may fail when their contacts have eroded to such a degree that they cannot effectively complete a circuit, or when the erosion has changed the physical shape of the contact such that the mechanical operation of the switch is interrupted. Once a contact has eroded to the point at which further use risks injury to personnel or machinery, known as the "critical point," a contact's useful life is over.

Because arcing and erosion cannot be eliminated, standard industry practice is such that switches are almost always designed to allow replacement of the contacts. It is typically less expensive to replace worn contacts than to replace an entire switch when the contacts have eroded to the critical point or close thereto. As a result, users of switches must monitor the erosion of the contacts to recognize when the predetermined critical point is approaching or has been reached. Replacing worn contacts at or before the critical point is important because contacts used past that point continue to erode and may cause the switch to fail. A switch failure can have a negative or catastrophic effect on equipment and presents a danger to personnel. Further, such a switch failure can reduce the confidence of integrity and stability of a respective regional grid, which can have a material financial and other such effects on residential, commercial, and institutional users of that grid. On the other hand, replacing contacts before the end of their useful life increases material and labor costs.

There is a large expense associated with electrically isolating, or de-energizing, and physically inspecting high voltage electrical equipment to determine the extent of wear or erosion of the contacts. This expense is compounded by the necessity of removing, storing, and processing a large quantity of oil, sometimes up to 1000 gallons. Contacts are often replaced early due to the difficulty of predicting the rate of erosion from one maintenance cycle to the next. The expense of inspecting the contacts is often so great that typically maintenance departments change some of the contacts during every inspection, even though the contacts may have months or more of useful life remaining. Properly matching the timing of inspection with the end of the useful life of the contacts would thus advantageously result in a cost savings, and likely reduce the overall cost of ownership for a utility's grid.

One means or process or method commonly used to monitor electrical equipment performance, and identify equipment requiring maintenance, is to perform or conduct a Dissolved Gas Analysis (DGA). The DGA process involves extracting a sample of the oil surrounding the contacts and, by using gas chromatography, analyzing the oil for the presence and amount of certain gases dissolved within this insulating oil. The presence of certain gases is indicative of various types of events that may be occurring within the equipment. For example, a high level of methane or ethane dissolved in the oil would be indicative of excessive heating within load tap changers and transformers whereas the amount of acetylene would have a corresponding relationship with the amount of arcing that is occurring. The DGA method of monitoring, however, lacks the precision necessary to determine the proper timing of contact replacement, as the presence of dissolved gases related to erosion has no correlation to the amount or extent of erosion of the contacts.

There is accordingly a need to provide a method and apparatus for the detection of the extent of electrical contact erosion, or wearing, that is inexpensive and may be used by personnel on-site as well as in the laboratory.

SUMMARY OF INVENTION

The invention relates to an improved sacrificial electrical contact or interrupter assembly component. At least a portion of the electrical contact or interrupter assembly component, or a cavity defined therein, comprises a fluorescent trace material. At least a portion of the fluorescent trace material is exposed or released, indicating a degree of component wear.

In one aspect of the invention, a method and apparatus are provided for detecting the exposed or released trace material.

In yet another aspect of the invention, a trace material is provided within certain components of the electrical switching mechanism and, upon wear, may be released or exposed into the surrounding medium and monitored to detect or indicate component wear.

BRIEF DESCRIPTION OF DRAWINGS

For a more complete understanding of the present invention, and the advantages thereof, reference is now made to the following descriptions taken in conjunction with the accompanying drawings, in which:

For a more complete understanding of the present invention and the advantages thereof, reference is now made to the following description taken in conjunction with the accompanying drawings, in which:

FIG. 3a is a partial section of a contact assembly containing a cavity and trace material;

FIG. 3b is a partial section of a contact assembly that has suffered erosion due to arcing;

FIG. 4a is a top view of a baffle plate;

FIG. 4b is a side view of a baffle plate, taken along line 4b—4b of FIG. 4a;

FIG. 11b is a top view, in partial section, of the remote optical access port of FIG. 11a, taken along line 11b—11b of FIG. 11a;

FIG. 12 is an emission spectra of oil samples performed during testing of one preferred embodiment of the present invention;

FIG. 13 is an emission spectra of oil samples at emission minima performed during testing of one preferred embodiment of the present invention;

FIG. 14 is an emission spectra of Opacity 6 oil with various concentrations of a trace material performed during testing of one preferred embodiment of the present invention;

FIG. 15 is an emission spectra of dilute oil samples performed during testing of one preferred embodiment of the present invention; and FIG. 16 is the strength emission of a trace material showing the concentration versus emission detectability performed during testing of one preferred embodiment of the present invention.

DETAILED DESCRIPTION OF THE INVENTION

Although the invention has been described with reference to specific embodiments, these descriptions are not meant to be construed in a limiting sense. Various modifications of the disclosed embodiments, as well as alternative embodiments of the invention will become apparent to persons skilled in the art upon reference to the description of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

It is therefore contemplated that the claims will cover any such modifications or embodiments that fall within the true scope of the invention.

Figure 1:
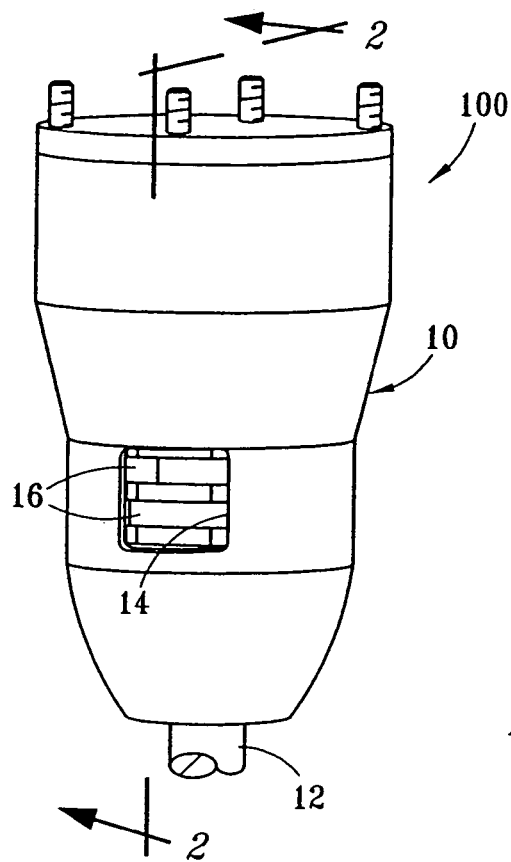
FIG. 1 is a perspective view of an interrupter assembly that may be used within a typical circuit breaker.

FIG. 1 shows an interrupter assembly 100 that may be used as part of a circuit breaker (not shown), for example. Interrupter assemblies generally are well-known in the art. The interrupter assembly 100 includes an interrupter shell 10 surrounding a male contact assembly 12 and a female contact assembly (not visible in FIG. 1). The interrupter shell 10 is preferably fabricated from a strong, non-conducting material such as phenolic cellulose tubing or fiberglass. The shell 10 wall is of sufficient thickness to contain the arc and to withstand the forces created by the arc-gas expansion during arcing. The interrupter assembly 10 is generally housed in an enclosure such as a tank or switch compartment, and surrounded by an insulating, non-conductive medium such as oil, air, or an inert gas. In one preferred embodiment of the present invention the non-conductive medium is a high dielectric insulating oil. Also shown in FIG. 1 is an exhaust port 14 and an assembly of baffle plates 16.

Figure 2:
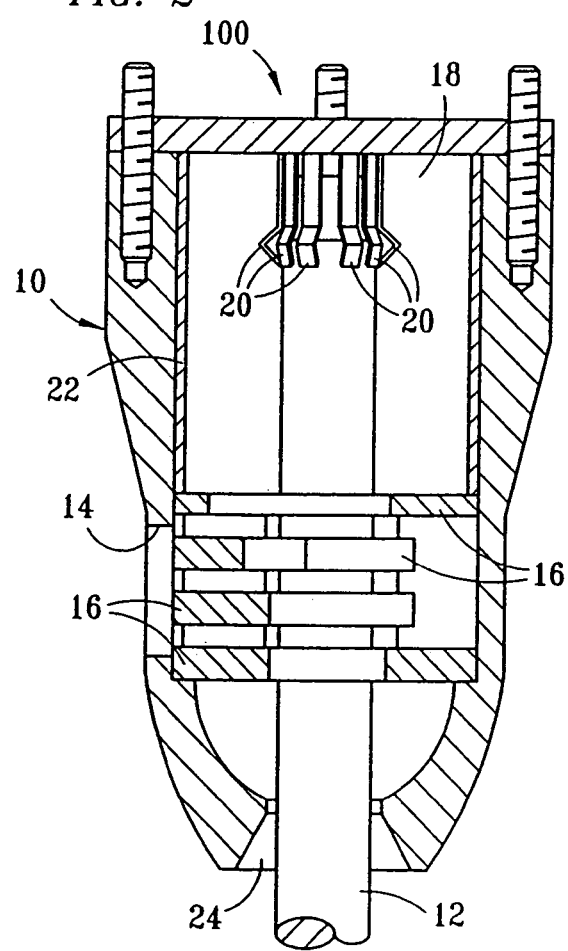
FIG. 2 is a section, taken along line 2—2 of FIG. 1, illustrating the position and arrangement of typical contact assemblies within the interrupter assembly.

In FIG. 2, a female contact assembly 18 is shown within the interrupter shell 10. The female contact assembly 18 comprises a plurality of contact segments 20, which are preferably arranged in a circular pattern. The contact segments 20 are preferably configured to engage the male contact assembly 12 and are preferably biased toward the male contact assembly 12 to promote electrical contact therewith.

The baffle plates 16 can be seen more clearly in FIG. 2. Four (4) baffle plates 16 are shown in this embodiment, although a greater or smaller number may be used and are described in more detail below, in connection with FIGS. 4a and 4b.

Under normal conditions, in one embodiment, the end of the contact assembly 12 extends into the interrupter assembly 100 via the opening 24 at the base of the interrupter assembly shell 10. During operation, the contact assembly 12 extends through the baffles 16, and penetrates into, or engages, the female contact assembly 18, allowing electric current to flow through the assembly. The contacts within the interrupter assembly are designed to open upon the occurrence of certain events, such as a fault, or short circuit, or a manual switch (not shown) being tripped. When the circuit breaker is tripped, the contact assembly 12 is rapidly retracted away from the female contact assembly 18 and from the interrupter shell 10. As the contact assembly 12 is pulled away from the female contact assembly 18, an arc will typically occur between the contacts.

FIGS. 3a and 3b show the contact assembly 12 of one embodiment in more detail. The contact assembly 12 may comprise a base 32 and a contact tip 34. The base 32 may be constructed from copper, although any electrically conductive material may be used. The contact tip 34 may be constructed from a material resistant to erosion from arcing, such as a tungsten-based alloy. The contact assembly 12 may comprise one or more cavities 36, such as defined in the contact tip 34, but may alternatively be located elsewhere in the contact assembly 12, provided at least a portion of the cavity 36 is subject to exposure to the surrounding medium (not shown) as a result of erosion due to arcing. A trace material (not shown) is provided in the cavity 36. The trace material (not shown) may be injected into the cavity or the contact tip 34 may be brazed onto the base 32 so that a cavity 36 is created within which the trace material is contained.

As the interrupter assembly 100 is used, the contact tip 34 erodes due to arcing. When the contact tip 34 has eroded to the extent that it breaches the cavity 36, an opening 42 to the cavity is created, as shown in FIG. 3b. The trace material is then in contact with the surrounding medium, and at least a portion of the trace material is released from the cavity 36 into the surrounding medium. The surrounding medium is monitored for the presence of the trace material, the presence of which indicates that the contact assembly 12 requires replacement.

In another embodiment, the fluorescent trace material may, instead, be distributed within the material comprising the contact assembly 12, the contact tip 34, the base 32, or any portion of these components. In that case, the fluorescent trace material is released into the surrounding medium more gradually as the contact assembly 12, or applicable portion thereof, erodes. At least one point in the surrounding medium is then monitored until a sufficient quantity of trace material is detected to indicate that the contact assembly 12 should be replaced.

In one embodiment the trace material preferably comprises at least one fluorescent trace material. Fluorescent trace material refers to luminescence in which light of a visible color is emitted from a substance under stimulation or excitation by light or other forms of electromagnetic radiation or by certain other means. The fluorescent component emits electromagnetic radiation when it is "excited," that is, when it is exposed to incident electromagnetic radiation within a particular frequency range. The molecules comprising the fluorescent component absorb the incident electromagnetic radiation and then emit electromagnetic radiation, preferably of a different wave-length than that absorbed. Preferably, a fluorescent component is chosen with an excitation wave-length in the ultraviolet range and which emits light in the visible spectrum upon excitation. Choosing a fluorescent component with excitation and emission frequencies within these ranges makes detection simpler, because the electromagnetic radiation emitted by the fluorescent component may be readily distinguished from reflected electromagnetic radiation used for exciting the fluorescent component.

In one embodiment the fluorescent components comprising the trace material may be able to withstand the high temperatures involved in the brazing process, typically between 1000 and 1250 degrees Fahrenheit.

The fluorescent trace materials fluoresce when exposed, or excited, to incident electromagnetic radiation with a broad-band UV light source and emit in a range diverse to the incident background radiation of the insulating oil. Other fluorescent materials known to one of ordinary skill in the art may also be used as a trace material.

Semiconductor nanocrystal quantum dots ("nanocrystals," "quantum dots" or "nanocrystals quantum dots") are tiny crystals composed of periodic groups of II–VI, III–V, or IV–VI materials that range in size from 2–10 nanometers or roughly the size of 10 to 50 atoms in diameter. Due to the extremely small size of the nano-crystals, the optical, electronic, and chemical properties of the quantum dots are dominated by physical size and the chemistry of their surface. The diameters of the semiconductor nanocrystal quantum dots are, in fact, smaller than the Bohr radius of an electron-hole pair (exciton) formed through a photon interaction with the nanocrystal resulting in the quantum confinement effects. The results of quantum confinement are that the electron and hole energy states within the nanocrystals are discrete (similar to a 3-d spherical quantum well) where the electron and hole energy levels are a function of the quantum dot diameter as well as composition. The larger the nanocrystals become the smaller the difference between energy states. Because all optical and electronic properties are dependent upon the energy and density of electron states, the properties can be altered by engineering size and surfaces of these tiny structures. In effect, quantum confinement results in a controlled blue shifting of the bulk energy bandgap so that properties such as absorption onset and peak photoluminescence wavelength are size dependent. In a semiconductor nanocrystal quantum dot, strong absorption occurs at specific photon energies, at the expense of reduced absorption at other energies. In addition, quantum confinement effectively enhances many nonlinear effects due to a concentration of the oscillator strength into narrow wavelength bands. These properties include the non-linear refractive index (optical Kerr effect), non-linear absorption, quantum confined Stark effect, and other electro- and magneto-optic effects.

The following is a list of unique linear optical effects exhibited by semiconductor nanocrystal quantum dots:

Absorption Spectra of Quantum Dots

The absorption spectrum appears as a series of overlapping peaks that get larger at shorter wavelengths. Each peak corresponds to an energy transition between discrete electron-hole energy levels (exciton) within the nanocrystal. The nanocrystal will not absorb light that has a wavelength longer than that of the first exciton peak, also referred to as the absorption onset. At the short wavelength limit the absorption of the nanocrystals mimics that of a bulk semiconductor. Like all other optical and electronic properties, the wavelength of the first exciton peak (and all subsequent peaks) is a function of the composition and size of the nanocrystal. A smaller nanocrystal results in a first exciton peak at shorter wavelengths.

Photoluminescence Spectra of Quantum Dots

The wavelength at which the nanocrystals luminesce is directly related to the nanocrystal size and composition and hence the energy differences between electron states. By synthesizing a quantum dot of a given composition to a desired size, the emission wavelength can be chosen. The smaller the difference between the states, the "redder" the emission, thus small nanocrystals will emit "bluer" light and larger nanocrystals will emit "redder" light. There is a limit on how "red" or "blue" the luminescence can be tuned. As the nanocrystals grow in size they begin to appear more like a bulk semiconductor. Thus the "red" limit is ultimately constrained by the bulk bandgap energy. On the other hand there is a limit on how controllably small nanocrystals can be grown which results in a practical "blue" limit.

Quantum Dot Fluorescence I

The fluorescence wavelength can be tuned from the mid-infrared through the visible and into to the ultraviolet wavelength regime, depending on the size and composition of the material. Examples of quantum dot emissions include Cadmium Selenide from 450 nm to 650 nm and Lead Selenide from 900 nm–2000 nm. CdS (from 350 nm to 470 nm), CdTe (from 600 nm to 725 nm), and PbS (from 800 nm to 1600 nm).

Quantum Dot Fluorescence II

The peak photoluminescence wavelength is bell-shaped and occurs at a slightly longer wavelength than the lowest energy exciton peak (the absorption onset). An interesting property of semiconductor nanocrystal quantum dots is that the PL wavelength is independent of the wavelength of the excitation light, assuming that it is shorter that the wavelength of the absorption onset. The bandwidth of the photoluminescence spectra, denoted as the Full Width at Half Maximum (FWHM) is a function of the intrinsic linewidth of the nanocrystals and the size distribution of the population of nanocrystals within a solution or matrix material. Emission spectra broadening due to size distribution are known as inhomogeneous broadening and are the largest contributor to the FWHM. Narrower size distributions yield smaller FWHM. For CdSe a 5% size distribution corresponds to a 30 nm FWHM while in PbSe a 5% size distribution corresponds to a 100 nm FWHM.

Quantum Yield of Quantum Dots

The percentage of absorbed photons divided that result in an emitted photon is called Quantum Yield (QY). The QY is a function of the relative influences of radiative recombination (producing light) and nonradiative recombination mechanisms (which produce no light). Nonradiative recombination, which is much faster than radiative recombination, largely occurs at the nanocrystal surface and is therefore greatly influenced by the surface chemistry. It is known that capping the nanocrystal with a shell of an inorganic wide band semiconductor reduces nonradiative recombination and results in brighter emission. It has also been demonstrated that different surface chemistries greatly affect QY. For example thiols present on the nanocrystal surface are hole traps and reduce QY while amines are not resulting in brighter nanocrystals.

Molecular Coupling of Quantum Dots

Colloidally prepared nanocrystal quantum dots are free floating and can be coupled to a variety of molecules via metal coordinating functional groups. These groups include but are not limited to thiol, amine, nitrile, phosphine, phosphine oxide, phosphonic acid, carboxylic acid or others ligands. This ability greatly increases the flexibility and application in which quantum dots can be used. By using the correct molecules on the surface, the quantum dots can suspend in nearly any solvent, or be implemented in a variety of inorganic and organic films. In addition the surface chemistry can be used to effectively alter the properties of the nanocrystal including brightness, and electronic lifetime.

In one preferred embodiment, the trace material comprises certain semiconductor nanocrystals quantum dots.

FIGS. 4a and 4b illustrate one configuration of a baffle plate 16 that may be used in an interrupter assembly 100. The baffle plate 16 controls the flow of gases produced as a result of arcing ("arc-gases")(not shown) through the arc-gas exhaust port 14 and aids in constricting the arc (not shown) and directing the arc into the exhaust port 14. The arc and arc gases are directed through a reduced section channel 44 defined in the baffle plate 16, which is directed toward the exhaust port 14. The exhaust port 14 is directed toward an arc barrier chamber, which prevents the arc and arc-gasses from contacting the tank, or switch compartment, or other nearby components within the equipment. There is preferably either a notch 48 or a hole (not shown) defined in each baffle plate 16, which allows the contact assembly 12 to extend through the baffle plates 16.

The baffle plates 16 may be constructed from a non-conductive material with sufficient strength to withstand the high forces created by arcing. Additionally, the baffle plates 16 may be preferably constructed from a material that will at least partially vaporize when exposed to arcing so that any material which is released from the baffle plates 16, as a result of arcing, will be vaporized, rather than remain as particulate debris within the surrounding medium. The baffle plates 16 may be constructed from homogeneous cellulose or reinforced melamine resin. Other materials known to one of ordinary skill in the art may be used to construct the baffle plates 16.

Because of the tendency of baffle plates 16 used in an interrupter assembly 100 to experience wear over time as a result of arcing, it is necessary to replace the baffle plates 16 before they become so worn that the baffle plates 16 no longer function effectively. In order to determine the optimal replacement time without necessitating disassembling the interrupter assembly 100 for visual inspection, one may use a trace material in the baffle plates 16, similar to the use described above in connection with the contact assembly 12.

As shown in FIG. 4a, a cavity 46 is defined in the baffle plate 16, preferably near the channel 44 and the exhaust port 14. The cavity 46 may be created by machining a shallow depression in the underside of the baffle plate 16. Another method would be to create a cavity by drilling a cylindrical hole from a point remote to the area that would be subject to arcing. A trace material (not shown) is provided in the cavity 46. The trace material is preferably a fluorescent trace material as described herein, although other trace materials may alternatively be used. A cover 47 or plug is preferably provided to seal the cavity 46. The cover 47 or plug preferably is comprised of the same material as that used for construction of the baffle plates 16. As the baffle plates 16 experience wear as a result of arcing, eventually an opening (not shown) to the cavity 46 will develop, allowing at least a portion of the trace material to escape into the surrounding medium. The surrounding medium is monitored for the trace material, the presence of which indicates at least one baffle plate 16 is in need of replacement.

Alternatively to providing the trace material in one or more cavities, the material may, instead, be distributed within the material comprising the baffle plate 16, or any portion of thereof. In such case, the trace material is released into the surrounding medium gradually as the baffle plate 16, or applicable portion thereof, erodes. At least one point in the surrounding medium is then monitored until a sufficient quantity of trace material is detected to indicate that at least one baffle plate requires replacement.

The trace material may comprise the same material used as a trace material in connection with the contact assembly 12. Alternatively, a different trace material may be selected so that, by identifying which trace material is present in the surround medium, the user may identify whether the contact assembly 12 or baffle plates 16 require replacement. Further, a non-fluorescent trace material may be used, provided an appropriate detection means is also used.

Figure 5:
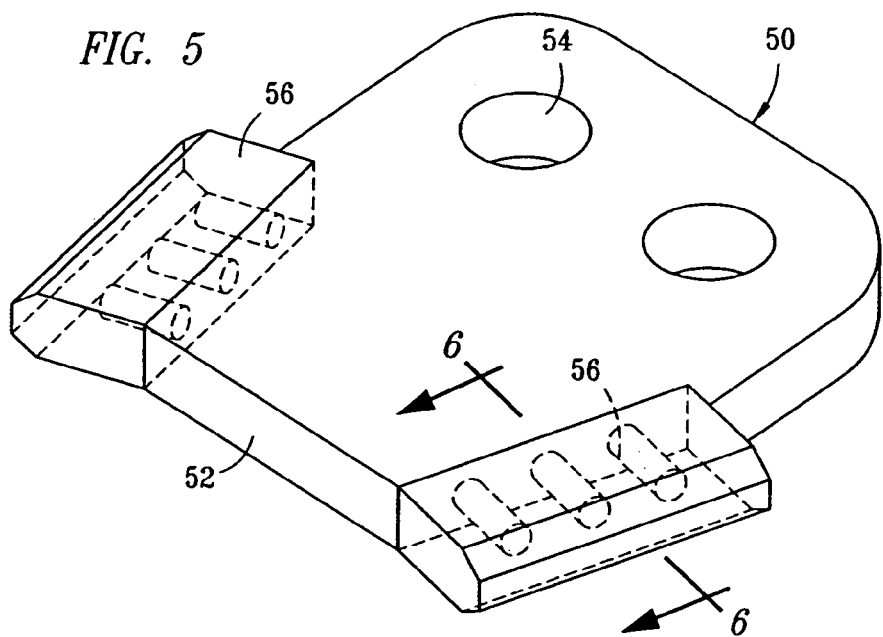
FIG. 5 is a perspective view of a contact assembly containing a cavity and trace material.

Shown in FIG. 5 is another embodiment of a contact assembly 50 including a cavity and trace material. Contact assembly 50 is of the type that may be used in a load tap changer selector switch that does not transfer or divert current during tap changing operations and therefore experiences arcing during the normal operation of a transformer (not shown). In a selector switch, one or more stationary contact assemblies 50 are provided for each of the taps of a secondary winding (not shown) in a transformer. A second part of the selector switch, the moving contact assembly (not shown), is used to conductively engage the contact assembly 50, thereby allowing selection of the secondary winding tap chosen by the user. The selector switch, of which the contact assembly 50 is a part, switches between taps while under load, causing arcing and erosion.

The contact assembly 50 includes a base 52 preferably made of copper, although any electrically conductive material may be used. The base 52 may be provided with one or more holes 54 for mounting to a selector switch. One or more contact tips 56 are bonded to and in electrical communication with base 54. The contact tips 56 are preferably made from a material that is conductive and resistant to erosion from arcing, such as a tungsten-based alloy. The contact tips 56 are preferably bonded to the base 52 by brazing. In another embodiment, the contact is fabricated entirely from tungsten-based alloy thereby requiring no brazing.

The contact tips 56 are provided with one or more cavities 58. Cavities 58 are formed in the contact tips 56 by machining prior to assembly by brazing or by drilling a cylindrical hole from a point remote to the area that would be subject to arcing such that the cavities 58 are sealed when the contact tips 56 are bonded to the base 52. After a cavity 58 is provided, a trace material (not shown) is inserted into the cavity 58, and the contact tip 56 is bonded to the base 52. The trace material is preferably as described above in connection with FIGS. 3a and 3b. In another embodiment, the trace material is inserted into the cavity prior to brazing.

Figure 6:
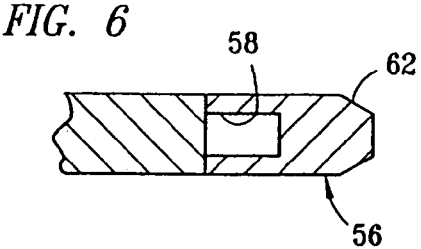
FIG. 6 is a partial section view, taken along line 6—6 of FIG. 5, showing the construction and assembly of the contact, cavity and trace material in greater detail.

Referring to FIG. 6, a contact tip 56 is shown as a partial section view along line 6—6 of FIG. 5. A partial representation of the base 52 is also shown. The contact tip 56 has a front edge 62, which is preferably beveled. Front edge 62 is the first part of the contact tip 56 to touch the second part of the selector switch when the switch closes, and it is the last part of contact tip 56 to separate from the opposite contact when the switch opens. Therefore, the front edge 62 is the surface of the contact tip 56 which is most subject to erosion from arcing.

As the contact assembly 50 is used, the contact tips 56 erode from arcing. When the contact tips 56 have eroded to a sufficient degree, the cavities 58 are opened. As a cavity 58 is opened, the trace material comes into contact with and is dispersed into the surrounding medium. When the presence of the trace material is detected in the surrounding medium, replacement of the contact assembly 50 is required.

Alternatively to providing the fluorescent trace material in one or more cavities, the material may, instead, be distributed within the material comprising the contact assembly 50, the contact tip 56, the base 52, or any portion of these components. In such case, the fluorescent trace material is released into the surrounding medium more gradually as the contact assembly 50, or applicable portion thereof, erodes. At least one point in the surrounding medium is then monitored until a sufficient quantity of trace material is detected to indicate that the contact assembly 50 should be replaced.

Figure 7:
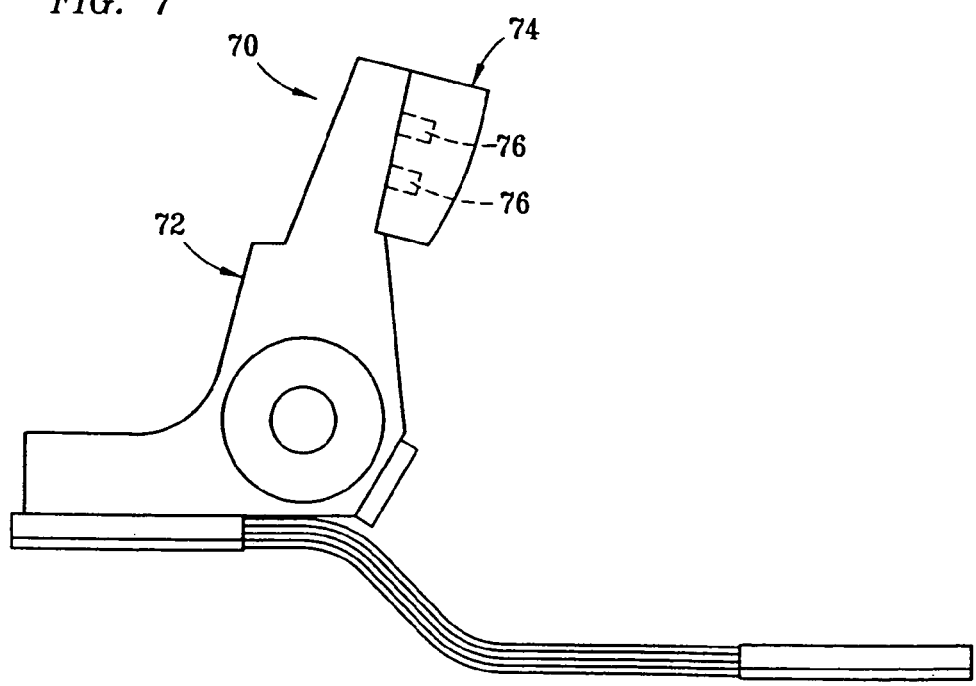
FIG. 7 is a side view of a transfer switch sacrificial contact assembly containing a cavity and trace material.

Turning now to FIG. 7, another embodiment of a sacrificial contact is shown. Contact assembly 70 is used in a high voltage load tap changer to transfer, or divert, the electrical current prior to movement of the selector switch, and is accordingly subject to accelerated arcing and erosion as it operates during each operation of the selector switch. Contact assembly 70 comprises a base 72 and a contact tip 74. Alternatively, the contact may be fabricated entirely from a tungsten-based alloy. The contact tip 74 is provided with one or more cavities 76. A fluorescent trace material (not shown) is inserted into the cavities 76 prior to brazing and/or the cavities created by machining prior to it being sealed when the contact tip 74 is brazed to the base 72 or by drilling a cylindrical hole from a point remote to the area that would be subject to arcing and a fluorescent trace material (not shown) is implanted into the cavities 76; or by any of the various other methods well known to those of ordinary skill in the art. The trace material is preferably as described above in connection with FIGS. 3a and 3b.

As the contact assembly 70 is used to create and break electrical circuits, erosion occurs. When the contact tip 74 is eroded to a sufficient degree, the cavities 76 are opened. As the cavities 76 are opened, the trace material comes into contact with and is dispersed into the surrounding medium. When the presence of the trace material is detected in the surrounding medium, replacement of the contact assembly 70 is indicated.

Alternatively to providing the fluorescent trace material in one or more cavities, the material may, instead, be distributed within the material comprising the contact assembly 70, the contact tip 74, the base 72, or any portion of these components. In that case, the fluorescent trace material is released into the surrounding medium more gradually as the contact assembly 70, or applicable portion thereof, erodes. At least one point in the surrounding medium is then monitored until a sufficient quantity of trace material is detected to indicate that the contact assembly 70 should be replaced.

Figure 8:
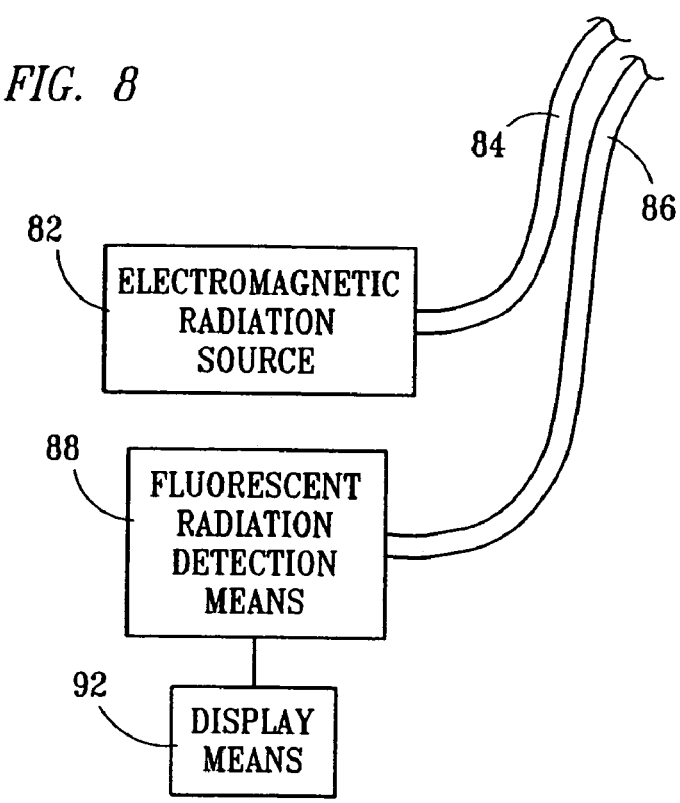
FIG. 8 is a schematic diagram of a fluorescent trace material monitoring or detecting system.

FIG. 8 is a schematic representation of a means for detecting a fluorescent material in a medium surrounding a contact assembly ("surrounding medium"). The detection means comprises an electromagnetic radiation source 82. The electromagnetic radiation source 82 generates electromagnetic radiation that is directed into the surrounding medium and used to excite any fluorescent trace material present in the surrounding medium. The electromagnetic radiation source 82 preferably generates electromagnetic radiation of a wave-length that is known to cause fluorescence in the particular fluorescent trace material being detected. As described above, such wave-length is preferably in the visible ultraviolet light range; however electromagnetic radiation of other frequencies may also be used.

Alternatively, a sample of the surrounding medium may be extracted as a sample and monitored for the presence of the trace material using an electromagnetic radiation source either in a laboratory or by a portable instrument used by on-site personnel.

Alternatively, the material may be monitored via an in-situ sensor embodied within or unique to the matrix of the fluorescent material, that transmits status to a receiving device to help assure monitoring.

Many sources of ultraviolet light are known and may be used as the electromagnetic radiation source 82. Examples include fluorescent lamps, incandescent lamps and xenon lamps. The electromagnetic radiation from the electromagnetic radiation source 82 is directed into the surrounding medium using an electromagnetic radiation transmission means 84. The electromagnetic radiation transmission means 84 preferably comprises an optically-transmissive conduit, such as a fiber optic cable. Alternatively, the electromagnetic radiation transmission means 84 may comprise a transparent or translucent window or lens (not shown). In another embodiment, the electromagnetic radiation source 82 may be installed in the equipment tank (not shown) or switch tank or compartment (not shown) within which the contact assembly is located so that a separate electromagnetic radiation transmission means 84 is unnecessary. In yet another embodiment, a sample of the surrounding medium is removed from the contact assembly housing and analyzed using an electromagnetic radiation source 82 by maintenance personnel or in a laboratory environment. Alternatively, an in-situ sensor within the fluorescent material itself may be used to transmit status to a receiving device.

Any fluorescent material present in the surrounding medium will emit its own electromagnetic radiation ("fluorescent radiation") in response to the electromagnetic radiation directed into the surrounding medium. Fluorescent radiation refers to electromagnetic radiation of any frequency that is produced in response to absorption of electromagnetic radiation, including by fluorescence, phosphorescence, or other wave-length specific processes.

The fluorescent radiation is directed via a fluorescent radiation transmission means 86 to a fluorescent radiation detection means 88. The fluorescent radiation transmission means 86 preferably comprises an optically-transmissive conduit, such as a fiber optic cable. Alternatively, the fluorescent radiation transmission means 86 may comprise a transparent or translucent window or lens (not shown). The fluorescent radiation transmission means 86 may comprise the same structure or a different structure as the fluorescent radiation transmission means 86. Most preferably, the fluorescent radiation transmission means 86 and the electromagnetic radiation transmission means 84 comprise a single optical fiber. Alternatively, the fluorescent radiation detection means 88 may be installed within the tank or switch compartment within which the contact assembly is located so that a fluorescent radiation transmission means 86 is unnecessary. Alternatively, a piezo-electric circuit that converts, amplifies and modulates the fluorescent radiation transmission may be used. Additionally, a sample of the surrounding medium may be removed from the contact assembly tank or switch compartment and analyzed using fluorescent radiation detection means 88 by on-site personnel or in a laboratory environment.

The fluorescent radiation detection means 88 may comprise any means that is useful for converting the fluorescent radiation into form usable for detection. Preferably, the fluorescent radiation detection means 88 comprises a photodiode (not shown) which converts the electromagnetic radiation into an electrical signal. Alternatively, the fluorescent radiation detection means 88 may comprise an amplifier (not shown) which increases the intensity of the fluorescent radiation to a level that may be visually detected. In another embodiment, sufficient fluorescent material may be used that the concentration of fluorescent material in the surrounding medium is high enough to produce visible light without amplification.

If the fluorescent radiation detection means 88 comprises a photodiode or similar device which converts the fluorescent radiation into an electrical signal, then the electrical signal thus created is transmitted to a display means 92. The display means may be as simple as an LED which emits light when a current is applied. Alternatively, the display means 92 may comprise an analog meter. In another alternative, the display means 92 may comprise a processor which converts the signal to a digital quantity able to be displayed on an LCD display, for example. In yet another embodiment, especially where the electromagnetic radiation source 82 and fluorescent radiation detection means 88 are installed on the exterior of the equipment tank or switch compartment, the display means 92 comprises a transmitter which transmits the detected information by low voltage electrical connection, radio frequency or other methods to a remote observation site (not shown). Alternatively, the concentration of material may be transmitted such that there is a color display or some other indicator level having corresponding significance to the monitoring personnel. Additionally, it is noted that in certain embodiments a display means is not necessary.

Figure 9:
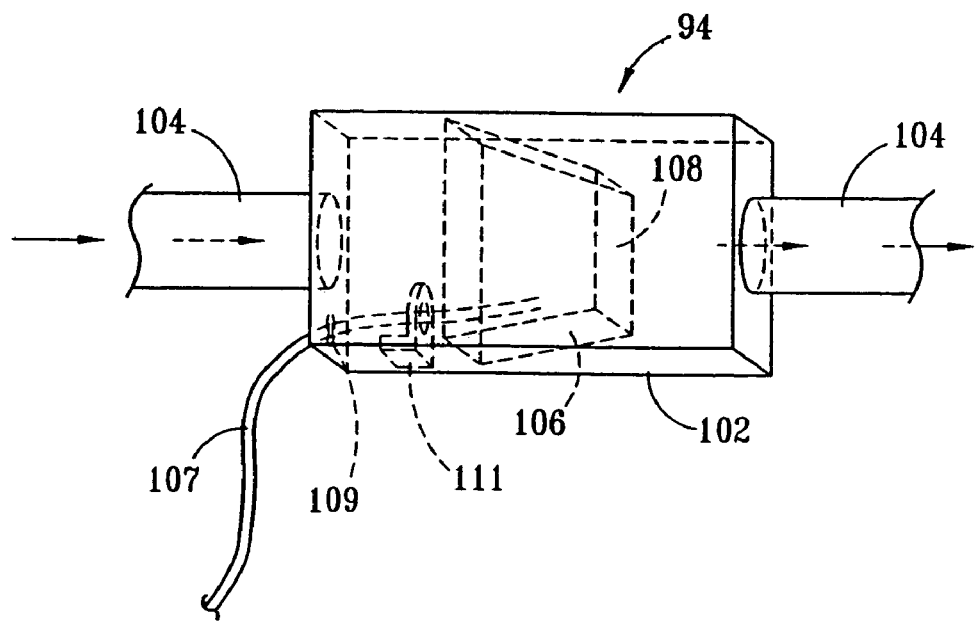
FIG. 9 is a perspective view of a particulate concentration or collection device employed in connection with monitoring for or detecting trace material.

Shown in FIG. 9 is a particulate concentration device 94 that may be used to aid in the detection of fluorescent trace material in the surrounding medium. The particulate concentration device 94 is configured for use in equipment having a forced-circulation system for filtering the oil surrounding the contacts. The particulate concentration device 94 is preferably located on a conduit which directs the flow of oil through the circulation system. A filter bed 106, constructed from a filtering material, substantially covers the area of oil flow through the particulate concentration device 94. The filter bed is preferably tapered in the direction of oil flow and preferably terminates at a collection surface 108.

As oil circulates through the particulate concentration device 94, some of the fluorescence trace material present in the oil, if any, will collect on the collection surface 108. In this embodiment, an optical transmission conduit 107 serves as the electromagnetic radiation transmission means 84 and the fluorescent radiation transmission means 86. The optical transmission conduit 107 extends through a wall of the particulate concentration device 94 to a position near the collection surface 108. A fitting 109 is provided in the wall of the particulate concentration device 94 to provide a seal around the optical transmission conduit 107. An end of the optical transmission conduit 107 is held in place by a first brace 111. Alternatively, a particulate concentration device 94 may be utilized with any trace material, not only a fluorescent trace material.

Electromagnetic radiation from the electromagnetic radiation source 82 is directed to the collection surface 108. Some of the fluorescent radiation produced by the fluorescent trace material on the collection surface 108 is directed through the fluorescent radiation transmission means 86 to a fluorescent radiation detection means 88.

Figure 10:
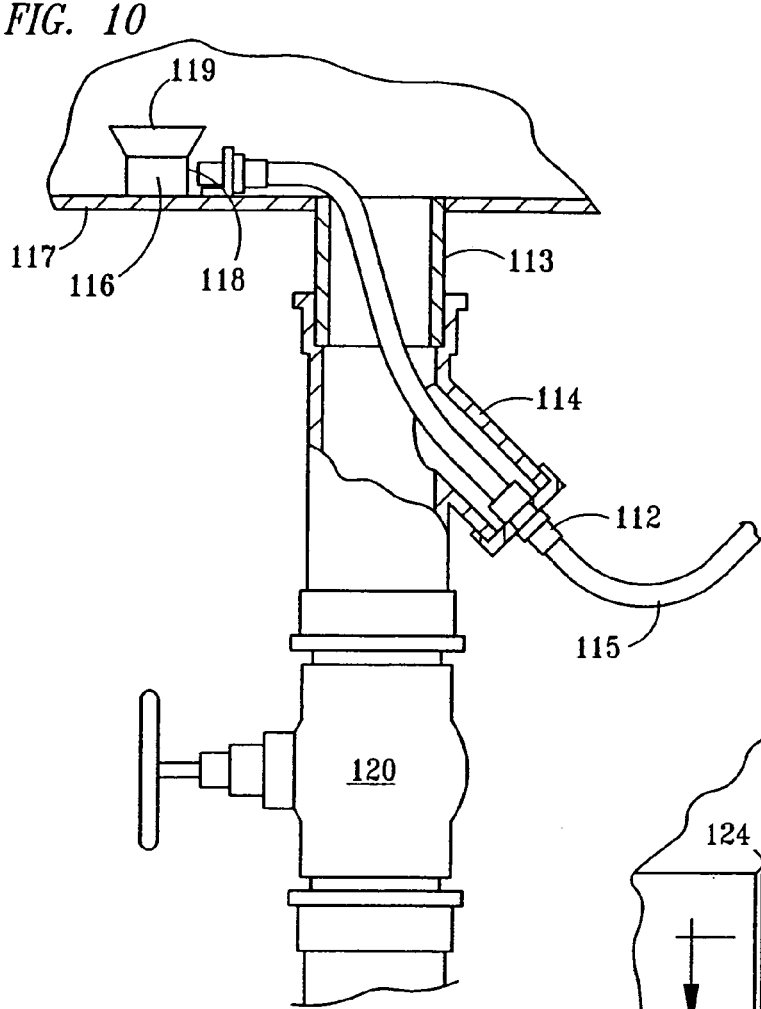
FIG. 10 is a side view, in partial section, of a drain assembly of a tank or switch compartment including an optically-transmissive conduit and port employed to monitor or detect trace material.

Shown in FIG. 10 is a particulate collection reservoir 116, which may be used in a tank or switch compartment as an alternative to the particulate concentration device 94 of FIG. 9, especially in a tank or switch compartment which does not include a forced-circulation filtration system. The particulate collection reservoir 116 is preferably located on a floor 117 of the tank or switch compartment, at a point at which fluorescent trace material is likely to settle after being released from a cavity in a contact assembly or baffle plate, for example. A particulate collection funnel 119 is preferably positioned over the particulate collection reservoir 116 to aid in the collection of the trace material; however, the particulate collection funnel 119 may alternatively be omitted.

Again in this embodiment, an optical transmission conduit 115 serves as an electromagnetic radiation transmission means 84 and a fluorescent radiation transmission means 86.

The optical transmission conduit enters the tank or switch compartment through a port 112, provided in a portion of a drain pipe 113, having an access opening 114. The access opening 114 is preferably nearer to the tank or switch compartment than a drain valve 120.

The end of the optical transmission conduit 115 is preferably positioned so that electromagnetic radiation from the electromagnetic radiation source 82 is directed towards a translucent or transparent observation wall 118 of the particulate collection reservoir 116. Any fluorescent trace material within the particulate collection reservoir 116 is excited by the electromagnetic radiation. A portion of the resulting fluorescent radiation, if any, is transmitted through the fluorescent radiation transmission means 86 to a fluorescent radiation detection means 88.

Figure 11A:
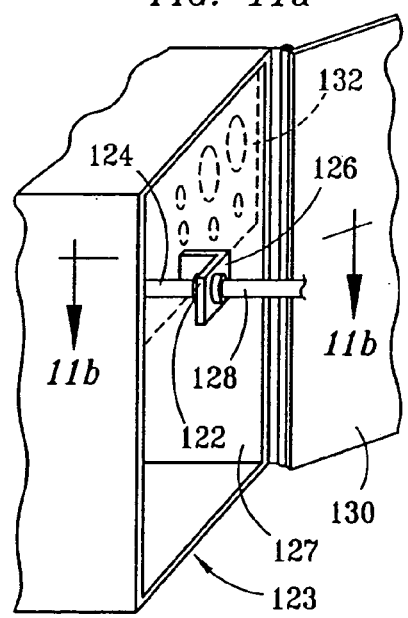
FIG. 11a is a perspective view of a remote optical access port within an equipment control cabinet.
Figure 11B:
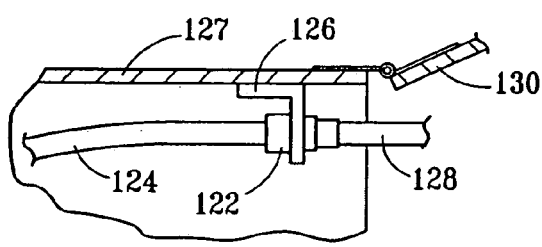
Figure 11C:
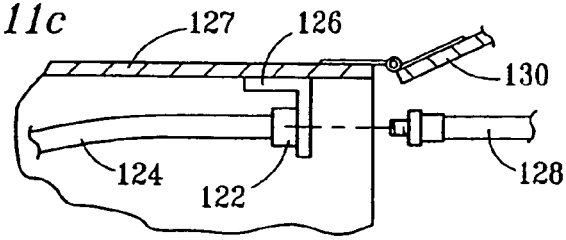
FIG. 11c is a top view, in partial section, of the remote optical access port of FIG. 11b, with a detached mobile transmission cable.

FIGS. 11a, 11b and 11c illustrate a remote access port 122 through which an electromagnetic radiation source 82 and fluorescent radiation detection means 88 may access the oil or other medium surrounding a switch. Preferably, one end of a permanent transmission cable 124 is connected to the remote access port 122, while an opposite end (not shown) is positioned at an appropriate place in the tank or switch compartment. The remote access port may be used in conjunction with the embodiments shown in either FIG. 9 or 10, or other embodiments.

The remote access port 122 is preferably mounted on a wall 127 of an equipment control cabinet 123, to allow for easy access by an operator. In FIG. 11a a generic instrument panel 132 is shown in broken lines to aid in interpretation of the drawing. The remote access port 122 is preferably held in place by a second brace 126. Alternatively, the remote access port 122 may be mounted to an existing instrument panel, such as generic instrument panel 132, for example. When not in use, the remote access port 122 is preferably enclosed behind a door 130 to the equipment control cabinet.

The remote access port 122 is configured to engage an end of a mobile transmission cable 128 and to allow transmission of electromagnetic radiation from the mobile transmission cable 128 to the permanent transmission cable 124 and vice versa. The end of the mobile transmission cable 128 is preferably configured for easy installation into and removal from the remote access port 122. In this embodiment, the mobile transmission cable 128 and permanent transmission cable 124 serve as an electromagnetic radiation transmission means 84 and a fluorescent radiation transmission means 86.

Experimental testing was performed using one preferred embodiment of the present invention with the results shown below.

Experiment 1

Six (6) oil samples were supplied ranging in opacity from Opacity 1, the clearest sample, to Opacity 6, the most opaque. The emission spectra of the six oil samples were measured using a PTI-500 fluorimeter in order to determine background emission levels. FIGS. 1 and 2 show the emission spectra of the 6 oil samples. FIG. 12 shows the full spectral range from 380 nm to 800 nm. FIG. 13 is the same spectra but focused on a more narrow spectral range of 600 nm–700 nm where the minimum background fluorescence was observed. Note the strong emission in the portion of the spectrum by the oil samples (wavelengths less than 560 nm).

Based on FIG. 13, it can be seen that the background emission of all the samples is lowest in the 620–680 nanometer range. In this embodiment a fluorescent trace material of CdSe/ZnS core/shell nanocrystals having hydrophobic surfactant layers, a peak emission wavelength of 626 nm, and a Full Width Half Maximum (FWHM) of 24.5 nm were chosen for the dilution and solubility experiments.

Experiment 2

Prior to dispersing the fluorescent trace materials in the Opacity 6 oil sample, 8.4 mg of fluorescent trace materials were separated from the toluene storage solvent through precipitation. Precipitation was achieved by adding methanol and centrifuging at 4000×G for 2 minutes. The supernatant was decanted 1 ml of the Opacity 6 oil sample (the most opaque oil sample) was added directly to the fluorescent trace materials pellet. The mixture was then sonicated for several seconds where the fluorescent trace materials were observed to quickly solvated into the oil matrix. The resulting oil/fluorescent trace materials solution was exposed to Ultraviolet illumination and a red glow, indicative of the fluorescent trace materials emission, was observed. The solution was then centrifuged again at 14000×G for 4 minutes. After centrifugation a large pellet of insoluble material was noted at the bottom of the centrifuge tube. Initially, it was believed that the fluorescent trace materials precipitated out of solution. However, under UV excitation the supernatant still exhibited the red glow indicating the presence of the nanocrystals, while the pellet had a faint blue glow, indicative of the oil.

Experiment 3

A control experiment was conducted on the Opacity 6 oil sample without fluorescent trace materials. The Opacity 6 oil sample was centrifuged at 14000×G for 4 minutes after which a large pellet was observed at the bottom of the centrifuge tube. An Ultraviolet light was used to illuminate the centrifuged ample and a faint blue glow was observed from the precipitated pellet.

Experiment 4

A further control experiment was conducted whereby the nanocrystals were added to the Opacity 1 oil sample (the clearest oil) in the same manner as Experiment 2. The resulting optically clear oil/nanocrystal solution was observed to have a red glow indicative of the nanocrystals under UV illumination. The sample was then centrifuged at 14,000×G. After centrifugation a precipitated pellet was not observed although the red glow of the nanocrystals was clearly seen in the oil solution under UV illumination.

Based on these results it can be concluded that the fluorescent trace material used in this embodiment is directly soluble in the oil itself and remains in solution even under extremely high centrifugal force. It was further concluded that the precipitate observed from the centrifugation from the most opaque oil sample was due to insoluble particles in the oil and not due to the fluorescent trace materials precipitating.

Experiment 5

To determine the minimal detectable concentration the emitting fluorescent trace materials were added to the highest opacity oil as described in Experiment 2. Successive dilutions of 8.4, 4.2, 2.8, 2.1, 1.4, 1.05, 0.84, 0.7, 0.6 mg/ml were made by adding more oil to the original oil/fluorescent trace material 1 concentration. The fluorescence of the oil/fluorescent trace material dilution series was measured with an Ocean Optics USB 2000 spectrometer with a fiber optic dip probe attachment. The dip probe is coupled to the Ocean Optics LS-450 light source with a 380 nm LED excitation source and the USB-2000 spectrometer as the detector platform via bifurcated optical fiber. Excitation light derived from the 380 nm LED propagates down the fiber to the oil/fluorescent trace material sample and the resultant fluorescent emission is directed back up the fiber to the spectrometer.

The dilution series samples were measured by directly inserting an Ocean optics dip probe (T300) into the oil/ fluorescent trace material solution. The dip probe was rinsed thoroughly between each measurement in order to minimize measurement error due to residual fluorescent trace materials adhering to the probe tip. Prior to measuring the fluorescent trace material doped samples, an oil background was run to minimize noise from the oil emission. FIG. 14 shows the emission spectra for the Opacity 6 oil/fluorescent trace material dilution samples. FIG. 15 is the same spectra that are focused in on the samples with the least fluorescent trace materials dispersed in the oil.

Based on emission data above it can be determined that the detectable concentration of fluorescent trace materials in the most opaque oil is >1 mg/ml (>4.4 nmol/ml). In FIG. 16 the adjusted maximum emission intensity at the fluorescent trace material peak wavelength is graphed as a function of fluorescent trace material concentration in the Opacity 6 oil sample. The adjusted maximum emission was taken to be the fluorescent emission at 626 nm minus the background signal (taken as an average between 480 and 570 nm).

The emission of 6 oil samples with varying opacity was measured. From these results it was noted that the minimum fluorescent light emission from the all oil samples occurs between 620–680 nm. Fluorescent trace materials with a fluorescent light emission peak at 626 nm (within the background light emission minima) were successfully solvated into high and low opacity oil samples and observed to glow a characteristic red. The fluorescent trace materials remained in solution even under high centrifugal forces indicating that the fluorescent trace materials will not precipitate out of the oils over long periods of time when used in power equipment. The fluorescent light emissions of varying concentrations of fluorescent trace materials solvated in the Opacity 6 oil samples (the highest opacity oils) were measured by a fiber optic dip probe coupled to a 380 nm illumination source and a spectrometer. Fluorescence of the fluorescent trace materials in the high opacity oil was measurable to a concentration of ~1 mg/ml (4.4 nmol/ml). Clearer oil samples with less contamination would require less fluorescent trace materials in solution for fluorescence detection.

Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered obvious and desirable by those skilled in the art based upon a review of the foregoing description of preferred embodiments. Many other forms of switches and other electrical contacts are known in the art and could be used in conjunction with features of the invention. Accordingly, it is appropriate that the appended claims be construed broadly and in a manner consistent with the scope of the invention.

What is claimed is:

1. A method for determining erosion of a contact assembly, the method comprising:
    providing a fluorescent trace material within the contact assembly;
    allowing the contact assembly to be eroded until at least a portion of the fluorescent trace material is released into a surrounding medium; and
    monitoring at least one point in the surrounding medium to detect a quantity of fluorescent trace material dispersed into the surrounding medium as an indicator of erosion of the contact assembly.

2. The method of claim 1, wherein the fluorescent trace material is provided within a cavity defined in the contact assembly.

3. The method of claim 1, wherein the monitoring step further comprises the steps of:
    directing electromagnetic radiation into the surrounding medium; and
    sensing the amount of radiation emitted by the fluorescent trace material to determine the amount of fluorescent trace material in the surrounding medium.

4. The method of claim 3, wherein the electromagnetic radiation is ultraviolet radiation.

5. The method of claim 3, wherein the electromagnetic radiation has a wave-length of about 254 nm.

6. The method of claim 4, wherein the ultraviolet radiation is generated from a source located within an enclosure surrounding the electrical contact assembly.

7. The method of claim 6, wherein the ultraviolet radiation is generated from a source located in a fluorescent trace material detecting device.

8. The method of claim 1, wherein the step of monitoring the surrounding medium comprises the steps of:
    circulating the surrounding medium through a particulate concentration device;
    directing electromagnetic radiation onto the fluorescent trace material in the particulate concentration device; and
    detecting the level of fluorescent radiation emitted in response to the electromagnetic radiation.

9. The method of claim 8, wherein:
    the particulate concentration device comprises a transparent or translucent observation wall; and
    the electromagnetic radiation is directed through the observation wall to the fluorescent trace material.

10. A method for determining the presence of fluorescent material associated with wear of an electrical contact assembly, comprising the steps of:
    generating electromagnetic radiation;
    directing the electromagnetic radiation to fluorescent material indicating wear of the contact assembly;
    detecting the amount of fluorescent radiation generated by the fluorescent material in response to the electromagnetic radiation; and
    determining a level of wear of the electrical contact assembly from the amount of fluorescent radiation detected.

11. A method for determining the level of a fluorescent trace material present in a medium surrounding an electrical contact assembly, comprising the steps of:
    circulating the surrounding medium through a particulate concentration device containing a collection surface;
    directing electromagnetic radiation to the particulate concentration device; and
    detecting the amount of fluorescent radiation generated by the fluorescent trace material collected by the particulate concentration device in response to the electromagnetic radiation.

* * * * *